United States Patent

Douglas

[11] Patent Number: 5,925,008
[45] Date of Patent: Jul. 20, 1999

[54] APPARATUS AND METHOD FOR SPLINTING AN APPENDAGE

[76] Inventor: John C. Douglas, 2714 Hafton Rd., Columbus, Ohio 43204

[21] Appl. No.: 08/925,036

[22] Filed: Sep. 8, 1997

[51] Int. Cl.⁶ .............................. A61F 5/00; A61F 13/00; A61F 5/37
[52] U.S. Cl. .................................. 602/22; 602/6; 602/61; 128/880
[58] Field of Search .............................. 602/5, 6, 12, 20, 602/22, 60–63, 75; 128/880

[56] References Cited

U.S. PATENT DOCUMENTS

| | | | |
|---|---|---|---|
| 4,143,653 | 3/1979 | Wichman | 602/22 |
| 4,161,175 | 7/1979 | Bentele | 128/87 A |
| 4,423,720 | 1/1984 | Meier et al. | 602/26 |
| 4,441,489 | 4/1984 | Evans et al. | 128/77 |
| 4,476,857 | 10/1984 | Levine | 602/20 |
| 4,489,716 | 12/1984 | Blackwood et al. | 602/20 |
| 4,781,178 | 11/1988 | Gordon | 602/22 |
| 4,798,200 | 1/1989 | Warthen et al. | 602/6 |
| 5,183,458 | 2/1993 | Marx | 602/22 |
| 5,230,699 | 7/1993 | Grasinger | 602/22 |
| 5,399,153 | 3/1995 | Caprio, Jr. et al. | 602/26 |
| 5,681,269 | 10/1997 | Basaj et al. | 602/22 |
| 5,695,452 | 12/1997 | Grim et al. | 602/26 X |
| 5,711,312 | 1/1998 | Staudinger | 128/845 |

Primary Examiner—Richard J. Apley
Assistant Examiner—Denise Pothier
Attorney, Agent, or Firm—Standley & Gilcrest

[57] ABSTRACT

An orthopedic device, particularly suited for treating mallet deformities, which has a strip of material having a body portion and a first, second, and third strap that are preferably connected to the body portion; and a splint having a first and second end portion. The splint is secured to a top side of the body portion of the strip of material so that when the strip of material is wrapped around an injured appendage, or finger, the first strap engages the first end of the splint and the second strap engages the second end of the splint. The third strap is also wrapped around the injured appendage and provides additional support to the orthopedic device of the present invention. It is also preferred that the splint be bent between the first and second end portions so that the appendage will be held in a hyperextended position once attached to the appendage by the first and second straps. The splinting device of the present invention is easily applied and form-fitting allowing the easy removal and reuse of the device.

13 Claims, 5 Drawing Sheets

APPARATUS AND METHOD FOR SPLINTING AN APPENDAGE

BACKGROUND AND SUMMARY OF THE INVENTION

The present invention relates to a method and apparatus for splinting an appendage. More particularly, the present invention describes a method and apparatus for splinting a mallet deformity.

A mallet deformity results from an injury to the extensor tendon which is distal to the proximal interphalangeal joint (PIP joint). (This deformity is discussed in the book entitled "The Hand: Operative Plastic and Reconstructive Surgery", edited by Barron and Saad, and published by Churchill Livingston, 1980.) This injury results in the inability to flex the distal interphalangeal joint (DIP joint). The majority of mallet injuries (closed) can be treated with continuous splinting of the DIP joint for 6 to 10 weeks. It is also necessary for the DIP joint to be immobilized in a slight hyperextended position while allowing the PIP joint to flex.

As discussed, when treating mallet injuries, it is known to splint an appendage in a hyperextended position. However, known methods of splinting mallet injuries are uncomfortable and unduly restrict the patient's use of the injured finger. For example, U.S. Pat. No. 4,441,489 to Evans describes a splint for treating mallet injuries. Many patients who suffer a mallet injury prematurely cease to use their prescribed splint because of the discomfort caused by using the splint and due to the hassle of attending to the splint (i.e. removing the splint at regular intervals and reapplying it using new bandages and/or wraps). Accordingly, by not keeping the injured appendage in the prescribed hyperextended position, the duration of the healing process is prolonged and there is an increased chance of improper healing. Accordingly, the present invention provides a method and apparatus for splinting injured appendages that is comfortable, easy to apply, and is removable and reusable. Accordingly, the present invention will increase the chance of proper healing of the splinted appendage as it encourages the patient to use the splint for the entire prescribed period.

The splinting device of the present invention is preferably comprised of:
a strip of material having a body portion and a first, second, and third strap that are preferably connected to the body portion; and a splint having a first and second end portion. The splint is secured to a top side of the body portion of the strip of material so that when the strip of material is wrapped around an injured appendage, or finger, the first strap engages the first end of the splint and the second strap engages the second end of the splint. The third strap is also wrapped around the injured appendage and provides additional support to the orthopedic device of the present invention. It is also preferred that the splint be bent between the first and second end portions so that the appendage will be held in a hyperextended position once attached to the appendage by the first and second straps.

The splint device of the present invention is easily applied and form-fitting allowing for the easy removal and reuse of the device. Additionally, the ability to remove and reuse the orthopedic device of the present invention allows for accumulation of multiple devices for a particular patient. Accordingly, a patient may have one splint device for work, one for bathing and another for wearing around the house. Additionally, periodically changing between a patient's multiple orthopedic devices of the present invention, may relieve any discomfort which may arise from keeping the injured finger in one position for a significant length of time.

In addition to the features mentioned above, objects and advantages of the present invention will be readily apparent upon a reading of the following description.

BRIEF DESCRIPTION OF THE DRAWINGS

Novel features and advantages of the present invention, in addition to those mentioned above, will become apparent to those skilled in the art from a reading of the following detailed description in conjunction with the accompanying drawings wherein similar reference characters refer to similar parts and in which.

DETAILED DESCRIPTION OF PREFERRED EMBODIMENT(S)

The preferred system herein described is not intended to be exhaustive or to limit the invention to the precise forms disclosed. They are chosen and described to explain the principles of the invention, and the application of the method to practical uses, so that others skilled in the art may practice the invention.

Figure 1:
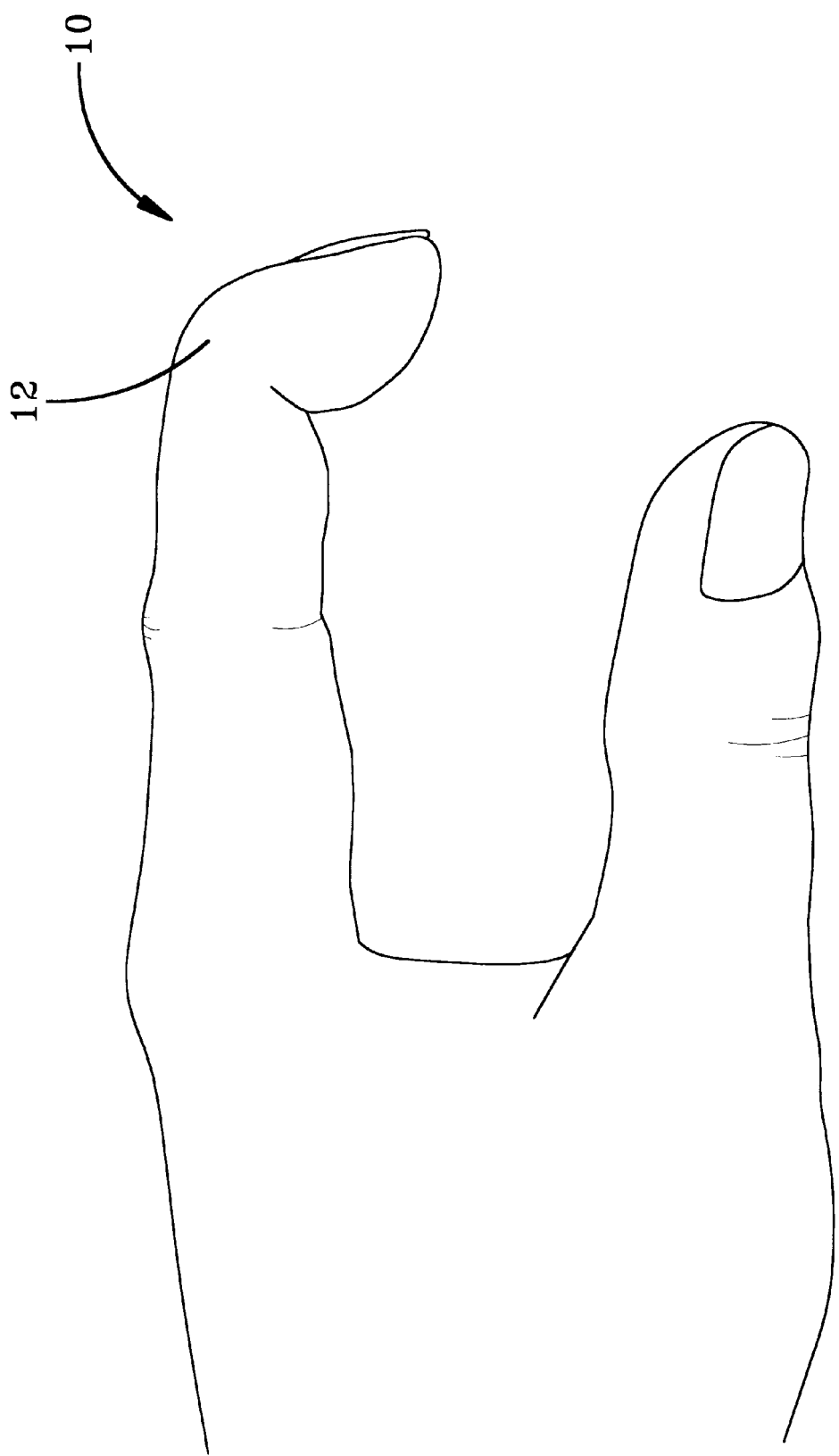
FIG. 1 illustrates an example of an appendage with a mallet deformity.

FIG. 1 illustrates an example of an appendage 10 with a mallet deformity. As illustrated the DIP joint 12 is dislocated and held in such position. The patient does not have the ability to flex the DIP joint 12 in this condition. Accordingly, for proper healing the appendage 10 must be splinted, preferably, to a slightly hyperextended position for a continuous period of between 6–10 weeks.

Figure 2:
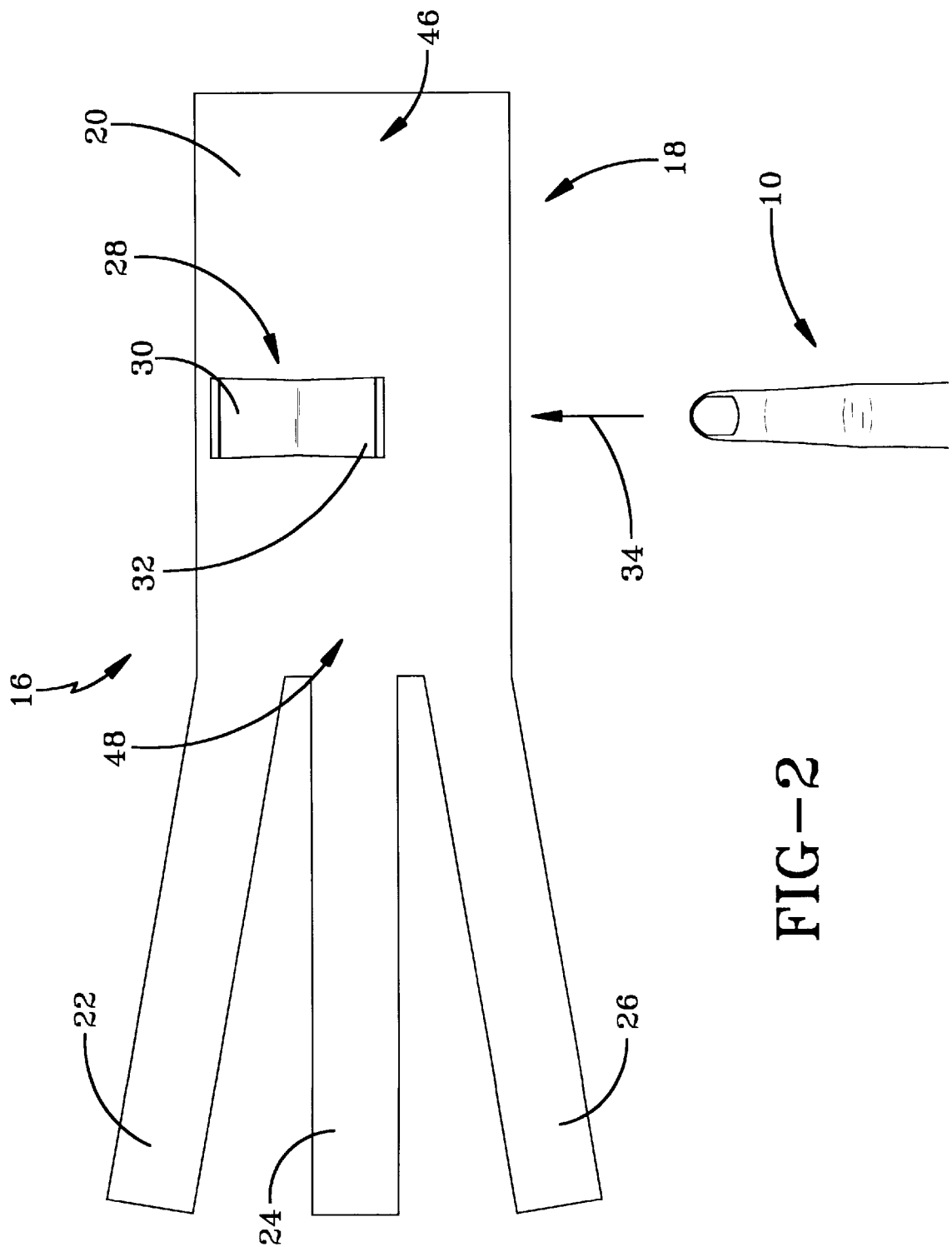
FIG. 2 illustrates a top plan view of the preferred embodiment of the orthopedic device according to the present invention.

FIG. 2 illustrates a top plan view of the preferred embodiment of the orthopedic device 16 according to the present invention. The orthopedic device 16 is shown in an unapplied or unassembled stage in FIG. 2. The orthopedic device 16 of the present invention is preferably comprised of a strip of material 18 having a body portion 20 and a first, second, and third strap 22, 24, 26 that are preferably connected to the body portion 20; and a splint 28 having a first and second end portion 30, 32. The splint 28 is secured to a top side of the body portion 20 of the strip of material 18 so that when the strip of material 18 is wrapped around the injured appendage 10, or finger, the first strap 22 engages the first end 30 of the splint 28 and the second strap 24 engages the second end 32 of the splint 28. The third strap 26 is also wrapped around the injured appendage and provides additional support to the orthopedic device 16 of the present invention. Arrow 34 points to the direction where the injured appendage 10 is to be inserted so that the strip of material 18 can be wrapped around the appendage 10.

In the preferred embodiment, the strip of material 18 is made from a self adhering stretch gauze. The gauze is a bandage-like material that adheres to itself but not to skin or hair. For example, the Maximum Support Self-Grip® Self Adhering Athletic Tape, manufactured by Dome Industries or Action Wrap Self Adhering Support Wrap manufactured by 3M may be used for the strip of material 18. The stretch gauze preferably conforms to the shape of the appendage 10. Accordingly, in the preferred embodiment the application of the orthopedic device does not require the use of any additional adhesive materials such as tape or the like. Alternatively, the strip of material 18 may also be comprised of a woven fabric or bandage.

Figure 3A:
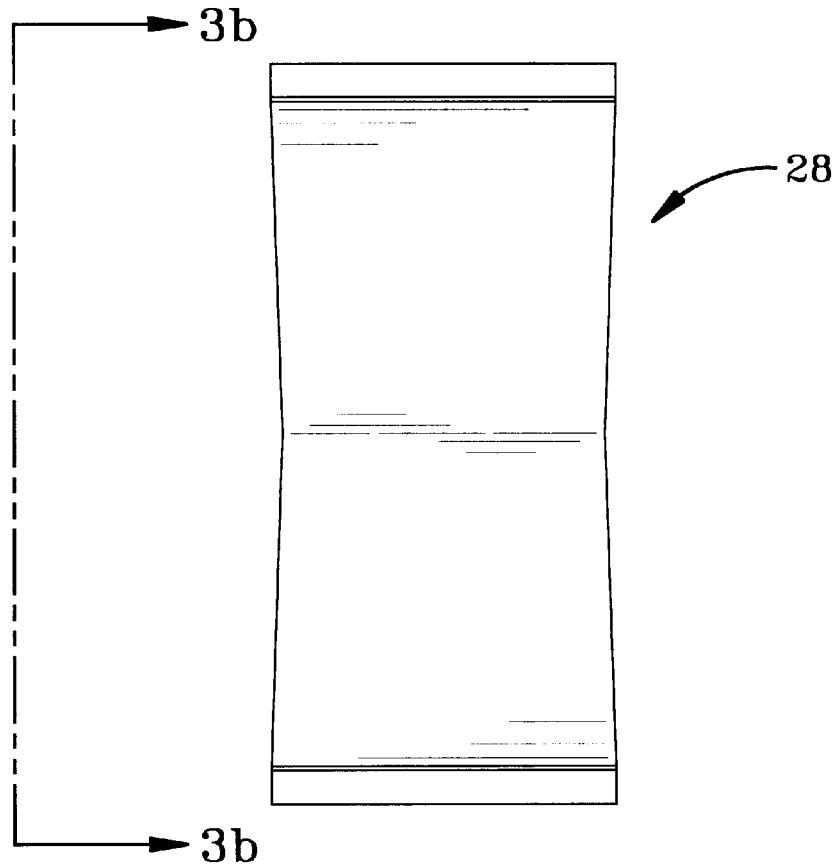
FIG. 3A illustrates a top plan view of the splint.
Figure 3B:
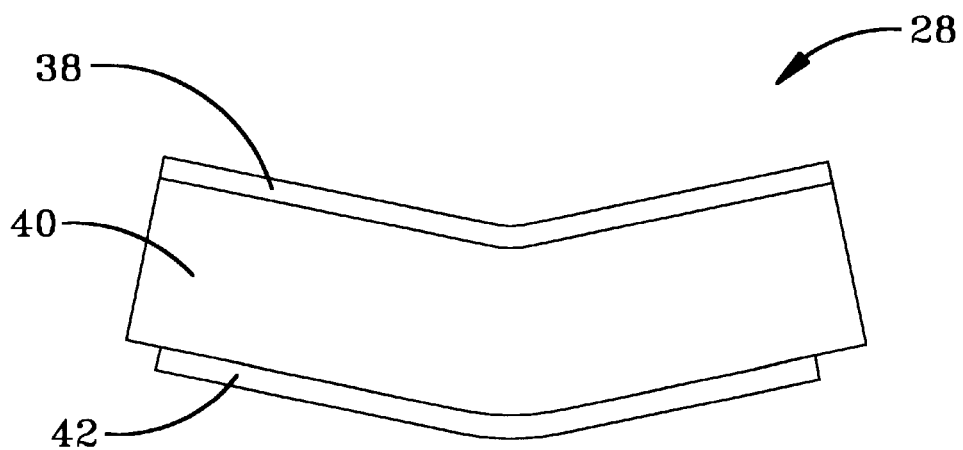
FIG. 3B illustrates a side elevational view of the splint as viewed from lines 3B—3B.

FIGS. 3A and 3B illustrate a preferred embodiment of the splint 28. FIG. 3A illustrates a top plan view of the splint 28. FIG. 3B illustrates a side elevational view of the splint 28 as viewed from lines 3B—3B. It is preferred that the splint 28 be comprised of a top aluminum layer 38; an intermediate foam layer 40 attached to the top aluminum layer 38; and an adhesive layer 42 for attaching the splint 28 to the strip of material 18. The adhesive layer 42 may be a velcro pad, a piece of two-sided tape, or any other adhesive material adapted to secure the splint 28 to the strip of material 18. In the preferred embodiment, the splint 30 is bent between the first and second portions 30, 32 so that the orthopedic device 16 hyperextends a tip portion of the injured appendage when the injured finger is splinted according to the present invention.

Figure 4:
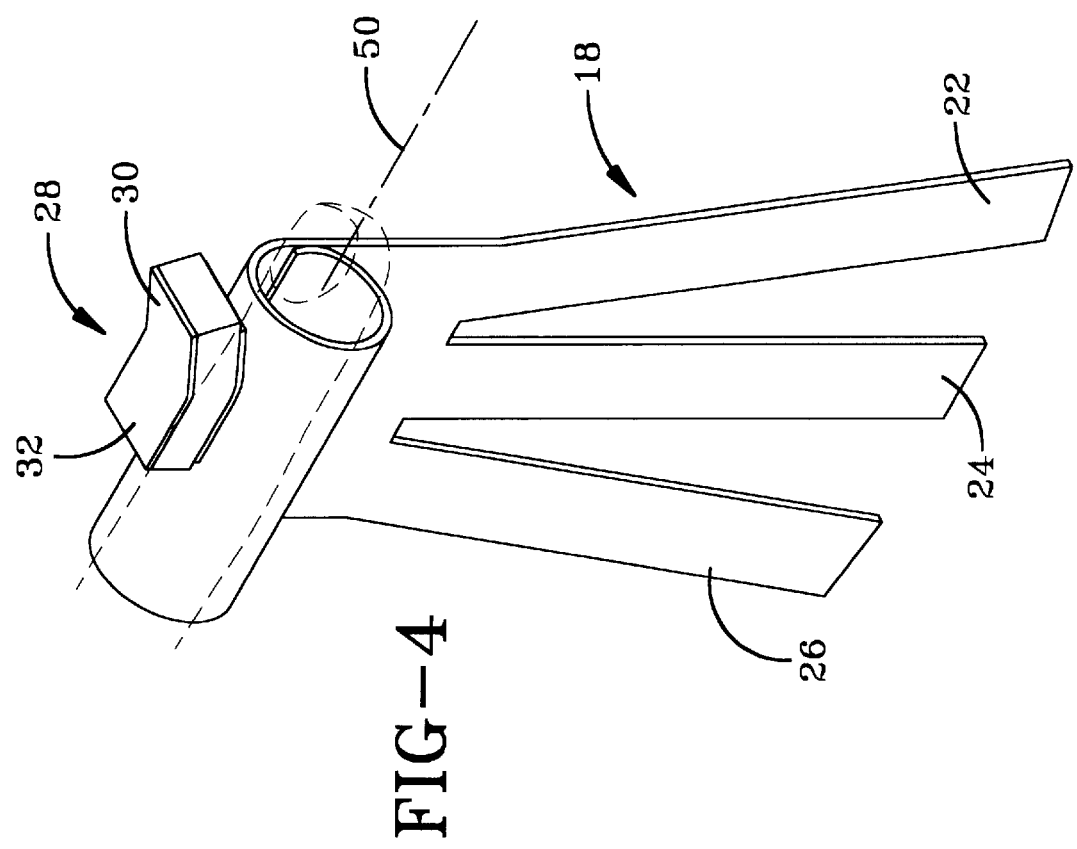
FIG. 4 illustrates the orthopedic device of the present invention partially wrapped around an injured appendage.

The following discussion describes the preferred method of using a preferred embodiment of the orthopedic device 16 of the present invention. As discussed, the orthopedic device 16 of the present invention is initially in an unassembled or unapplied state as shown in FIG. 2. To apply the orthopedic device 16 to an injured appendage 10, the injured appendage 10 is first placed under the device 16. It is preferred that the appendage be placed directly under the portion of the strip of material 18 where the splint 28 is attached (as shown by the arrow 34 in FIG. 2). A first end portion 46 of the strip of material 18 is then wrapped around the injured appendage 10. (The second end portion 48 of the strip of material 18 is attached to the straps 22, 24, 26.) Once the first end portion 46 of the strip of material 18 is wrapped around the appendage, the top of the injured appendage 10, at least, will be covered by the strip of material 18 (again, at this point, the splint 28 should be directly over the injured appendage 10—i.e. as illustrated in FIG. 4).

The straps 22, 24, 26 of the device 16 are then wrapped around the injured appendage 10, preferably wrapping around the appendage 10 in the opposite direction as the first end portion 46 of the strip of material 18. The first strap 22 is wrapped around the appendage 10 and the first portion 30 of the splint 28 securing the first portion 30 of the splint 28. In the preferred embodiment, the strip of material 18 is a self adhering gauze, thereby obviating the need for additional tape or bandages to secure the straps 22, 24, 26 to the other portions of the gauze. The second strap 24 is then wrapped around the appendage 10 and the second portion of the splint 28, securing the second portion 32 of the splint 28. In the preferred embodiment, the splint 28 is bent between the first and second end portions 30, 32 so that when the splint 28 is secured to the appendage 10 according to the present invention, the first end portion 30 of the splint 28 is at an angle relative to a horizontal axis as shown at 50. Accordingly, the wrapping and securing of the first and second straps 22, 24 to the first and second end portions 30, 32, respectively, of the splint 28 will place the tip of the injured appendage 10 in a hyperextended position. The third strap 26 can then be wrapped around the strip of material 18 to provide additional support for the splinted appendage.

Figure 6:
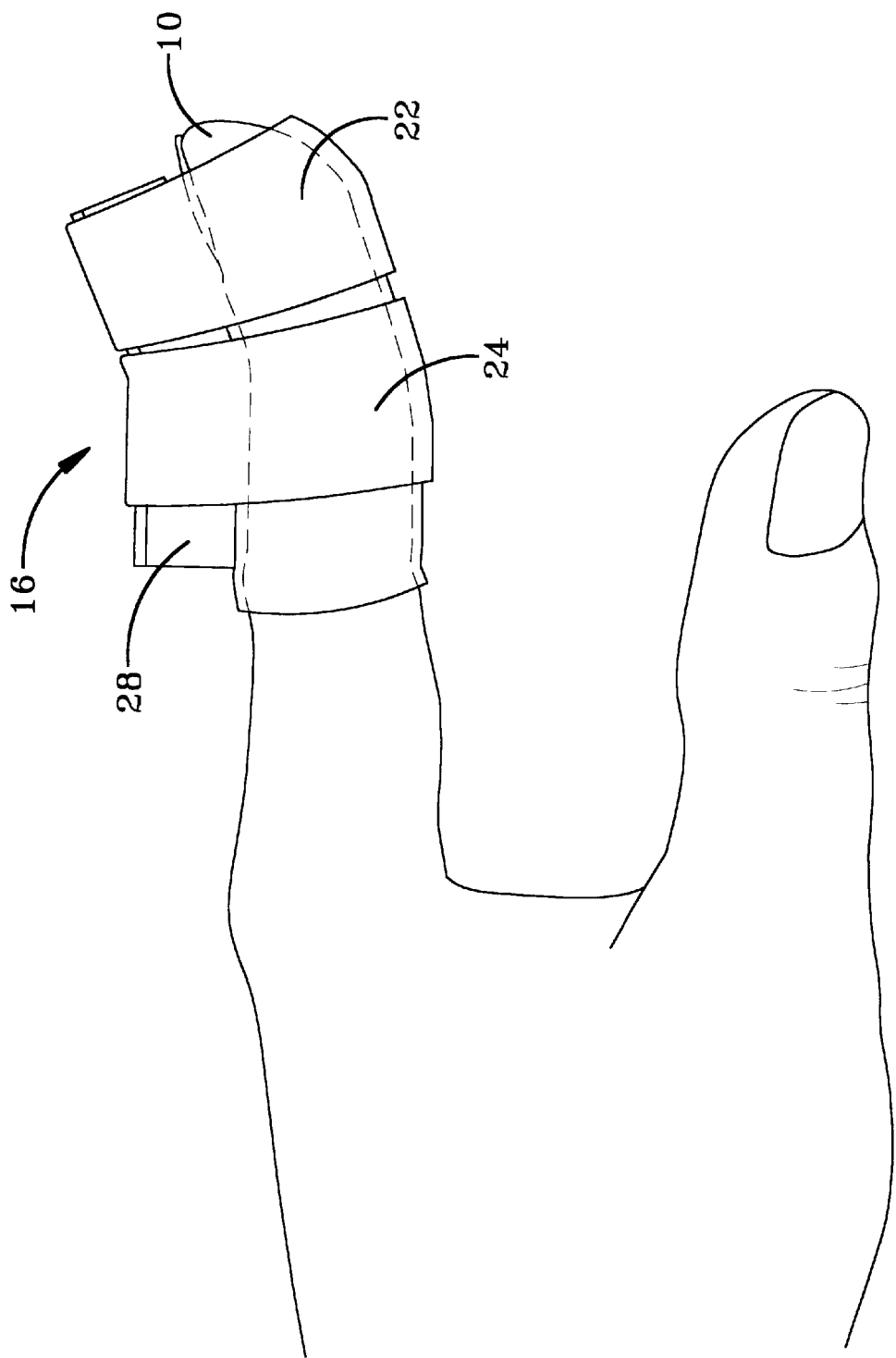
FIG. 6 illustrates an injured appendage that has been splinted according to a preferred embodiment of the present invention.

FIG. 6 illustrates an injured appendage 10 that has been splinted according to a preferred embodiment of the present invention.

Figure 5:
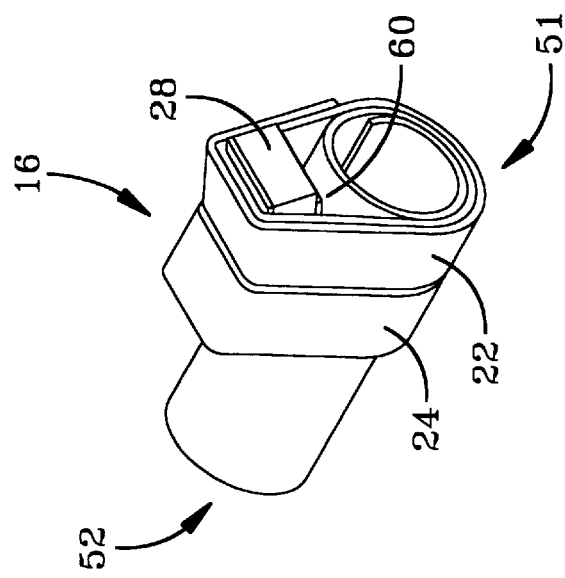
FIG. 5 illustrates an assembled orthopedic device of the present invention shown removed from the injured appendage.

The strip of material 18 is preferably of a construct that keeps its form once removed from the appendage (through use of a form fitting self-adhering stretch gauze). The orthopedic device in the assembled state, shown in FIG. 6, may be easily removed from injured appendage 10. FIG. 5 illustrates the orthopedic device 16 in an assembled state and shown removed from the injured appendage 10. As illustrated in FIG. 5, an assembled orthopedic device 16 according to the present invention is formed into a sleeve 51 having an aperture 52 for inserting the appendage 10 and where the sleeve 51 substantially surrounds the appendage 10. The splint 28 is attached to an outer surface 60 of the sleeve 51.

The patient may easily remove the orthopedic device 16 of the present invention to wash the injured appendage, to scratch the injured appendage, or to engage in an activity that is impeded by the presence of the splint on the appendage 10. At the desired time, the patient may easily replace the orthopedic device 16 onto the injured appendage 10 by simply slipping the appendage 10 into the sleeve 51 formed by the wrapped strip of material 18.

Figure 7:
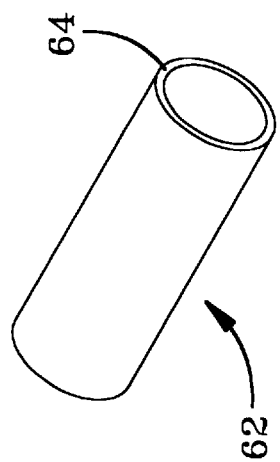
FIG. 7 illustrates a cushioned sleeve.

Additionally, in an alternative embodiment a cushioned sleeve 62 (FIG. 7) may be placed on the injured appendage 10 prior to wrapping the appendage 10 with the splinting device 16 of the present invention. The cushioned sleeve 62 is preferably made of a foam layer 64 for providing an extra layer of comfort for the patient.

The present invention to an orthopedic device, as described above, provides many advantages over known splinting techniques. The device 10 provides for the easy splinting of an injured appendage 10, while providing a form-fitted splint device that is easily removable and reusable. The ease of use and comfort level provided by the orthopedic device 16 of the present invention will increase the probability that the patient will splint an injured appendage 10 for the required prescribed time and thus increase the probability of having a properly healed appendage (i.e. finger, toe).

Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. An apparatus for splinting an appendage, comprising:
   a strip of material, said strip of material having a body portion and a first and second strap connected to said body portion, said strip of material having a top side and a bottom side;
   a splint hasting a first and second end, said splint secured to said top side of said body portion of said strip of material so that when said strip of material is wrapped around the appendage, said first strap engages said first end of said splint and said second strap engages said second end of said splint;
   wherein said splint is bent between said first and second end and is positionable on the appendage so that said apparatus hyperextends the tip of the appendage when said first strap engages said first end of said splint and said second strap engages said second end of said splint; and wherein said strip of material is sized to substantially surround the appendage when said first strap is engaged to said first end of said splint and when said second strap is engaged to said second end of said splint.

2. An apparatus according to claim 1, wherein said strip of material is further comprised of a third strap connected to said body portion of said strip of material, said third strap providing further support for said apparatus when wrapped around said appendage.

3. An apparatus according to claim 1, wherein said splint is comprised of:

a top aluminum layer;

an intermediate foam layer attached to said top aluminum layer; and an adhesive layer for attaching said splint to said strip of material.

4. An apparatus according to claim 1, wherein said strip of material is a self adhering stretch gauze.

5. An apparatus for splinting an appendage, comprising:

a first sleeve for substantially surrounding the appendage, said sleeve having an aperture for inserting the appendage and an outer surface and inner surface;

a splint attached to said outer surface of said first sleeve, said splint having a first and second portion;

a first strap wrapped around said first sleeve and said first portion of said splint;

a second strap wrapped around said first sleeve and said second portion of said splint;

wherein said first sleeve is sized to slidably engage to the appendage and wherein said first sleeve is sized to be completely removed from the appendage;

wherein said splint provides support to the appendage; and wherein said splint is bent between said first and second and is positionable on the appendage so that said apparatus hyperextends the tip of the appendage when said first strap engages said first portion of said splint and said second strap engages said second portion of said splint.

6. An apparatus according to claim 5, further comprising:

a cushioned sleeve substantially surrounded by said first sleeve.

7. An apparatus according to claim 5, wherein said splint is comprised of a:

a top aluminum layer; and an intermediate foam layer attached to said top aluminum layer.

8. An apparatus according to claim 7, wherein said splint is further comprised of:

an adhesive layer for attaching said splint to said first sleeve.

9. An apparatus according to claim 5, wherein said first sleeve is formed from a self-adhering wrap.

10. A method for splinting an appendage comprising the steps of:

providing a first strip of material having a first end portion and a second end portion, said second end portion being attached to a first and second strap;

wrapping said first end portion of said first strip of material around the appendage so that the top of the appendage is covered by said first strip of material;

bending a splint between the first and second end portion before attaching said splint to said first strip of material;

attaching said splint to said first strip of material, said splint having a first and second portion;

wrapping said first strap around the appendage and said first portion of said splint;

wrapping said second strap around the appendage and said second portion of said splint; and hyperextending a tip portion of the appendage.

11. A method for splinting an appendage comprising the steps of:

wrapping the appendage with a first strip of material;

providing a splint, said splint having a first portion and a second portion;

bending said splint between said first and second portion of said splint;

attaching said splint to said first strip of material;

wrapping a first strap around said first strip of material and said first portion of said splint;

wrapping a second strap around said first strip of material and said second portion of said splint; and wherein said attached splint causes a tip of the appendage to be hyperextended.

12. A method according to claim 11, further comprising the step of:

sliding said first strip of material and said attached splint off the appendage.

13. A method according to claim 11, wherein said first and second straps are attached to an end of said first strip of material.

* * * * *